US009750704B2

(12) United States Patent
Huatan et al.

(10) Patent No.: US 9,750,704 B2
(45) Date of Patent: Sep. 5, 2017

(54) HYDROCORTISONE CONTROLLED RELEASE FORMULATION

(71) Applicant: Diurnal Limited, Cardiff (GB)

(72) Inventors: Hiep Huatan, Maidstone (GB); Richard Ross, Sheffield (GB); Martin Whitaker, Nottingham (GB)

(73) Assignee: Diurnal Limited, Cardiff (GB)

( * ) Notice: Subject to any disclaimer, the term of this patent is extended or adjusted under 35 U.S.C. 154(b) by 360 days.

(21) Appl. No.: 14/374,179

(22) PCT Filed: Feb. 12, 2013

(86) PCT No.: PCT/GB2013/050311
§ 371 (c)(1),
(2) Date: Jul. 23, 2014

(87) PCT Pub. No.: WO2013/121184
PCT Pub. Date: Aug. 22, 2013

(65) Prior Publication Data
US 2014/0370113 A1   Dec. 18, 2014

Related U.S. Application Data

(60) Provisional application No. 61/599,704, filed on Feb. 16, 2012, provisional application No. 61/600,958, filed on Feb. 20, 2012.

(30) Foreign Application Priority Data

Feb. 13, 2012  (GB) .................................. 1202433.7

(51) Int. Cl.
*A61K 9/50* (2006.01)
*A61K 31/573* (2006.01)

(52) U.S. Cl.
CPC .......... *A61K 9/5026* (2013.01); *A61K 9/5078* (2013.01); *A61K 31/573* (2013.01)

(58) Field of Classification Search
CPC ... A61K 9/5026; A61K 31/573; A61K 9/5078
See application file for complete search history.

(56) References Cited

U.S. PATENT DOCUMENTS

| 4,552,872 | A | 11/1985 | Cooper et al. |
| 5,741,524 | A * | 4/1998 | Staniforth ............ A61K 9/2009 424/468 |
| 6,117,450 | A | 9/2000 | Dittgen et al. |
| 2008/0187586 | A1 | 8/2008 | Skrtic et al. |
| 2011/0159095 | A1 | 6/2011 | Huatan et al. |
| 2011/0189293 | A1* | 8/2011 | Padval ................ A61K 9/1652 424/489 |

FOREIGN PATENT DOCUMENTS

| EP | 2 143 424 A1 | 1/2010 |
| EP | 2 049 123 B2 | 8/2016 |
| GB | 2 292 079 A | 2/1996 |
| WO | WO 96/36319 A1 | 11/1996 |
| WO | WO 97/25980 A1 | 7/1997 |
| WO | WO 99/20255 A1 | 4/1999 |
| WO | WO 02/17887 A1 | 3/2002 |
| WO | WO 03/013476 A1 | 2/2003 |
| WO | WO 03/045356 A1 | 6/2003 |
| WO | WO 2005/025577 A1 | 3/2005 |
| WO | WO 2005/065692 A1 | 7/2005 |
| WO | WO 2008/059062 A1 | 5/2008 |
| WO | WO 2010/032006 A2 | 3/2010 |
| WO | WO 2010/113177 A2 | 10/2010 |
| WO | WO 2010/115615 A1 | 10/2010 |
| WO | WO 2011/057676 A1 | 5/2011 |
| WO | WO 2012/017385 A2 | 2/2012 |

OTHER PUBLICATIONS

Debono et al., "Novel Strategies for Hydrocortisone Replacement," *Baillieres Clin Endocrinol Metab.* 23:221-232, 2009.
Great Britain Combined Search and Examination Report for GB1202433.7, dated May 16, 2012.
Great Britain Combined Search and Examination Report for GB1302406.2, dated Apr. 26, 2013.
Great Britain Examination Report for GB1302406.2, dated Mar. 3, 2014.
Great Britain Combined Search and Examination Report for GB1408444.6, dated May 27, 2014.

* cited by examiner

*Primary Examiner* — Suzanne Ziska
(74) *Attorney, Agent, or Firm* — Klarquist Sparkman, LLP

(57) ABSTRACT

The disclosure relates to a pharmaceutical formulation comprising hydrocortisone and its use in the treatment of conditions that would benefit from a delayed release of hydrocortisone, in particular conditions such as adrenal insufficiency, inflammatory conditions and depression.

15 Claims, 7 Drawing Sheets

HYDROCORTISONE CONTROLLED RELEASE FORMULATION

CROSS REFERENCE TO RELATED APPLICATIONS

This is the U.S. National Stage of International Application No. PCT/GB2013/050311, filed Feb. 12, 2013, which was published in English under PCT Article 21(2), which in turn claims the benefit of Great Britain Application No. 1202433.7, filed Feb. 13, 2012, U.S. Provisional Application No. 61/599,704, filed Feb. 16, 2012, and U.S. Provisional Application No. 61/600,958, filed Feb. 20, 2012.

FIELD OF THE INVENTION

The disclosure relates to a pharmaceutical formulation comprising hydrocortisone and its use in the treatment of conditions that would benefit from a controlled release of hydrocortisone, in particular conditions such as adrenal insufficiency, inflammatory conditions and depression.

BACKGROUND TO THE INVENTION

In mammals the principle oscillator of circadian rhythms or central clock is in the suprachiasmatic nucleus. This master oscillator is responsible for the sleep-wake cycle and hormonal rhythms (e.g. cortisol and melatonin). It is recognised that peripheral tissues such as immune cells and the liver also have clock genes and their own molecular oscillating ability. Daily rhythms in gene expression, physiology and behaviour persist under constant conditions and must, therefore, be driven by self-sustained biological oscillators called circadian clocks. Circadian clocks can count time only approximately and must be adjusted every day by the photoperiod in order to be in harmony with the outside world.

There is a desire to develop drug delivery means to provide controlled drug release in particular in accordance with the circadian rhythm of a patient. There are a number of conditions that would benefit from this treatment regimen, for example adrenal failure, primary, secondary tertiary adrenal insufficiency and steroid withdrawal, inflammatory diseases such as rheumatoid arthritis and in the treatment of depression and related depressive illnesses including chronic fatigue and myalgic encephalitis (ME).

Adrenal failure occurs in approximately $1/10,000$ of the population. It may be due to either primary adrenal failure or secondary adrenal failure (which occurs due to pituitary failure which may be caused by a pituitary tumour or surgery). In primary adrenal failure, ACTH levels from the pituitary will be high and in secondary adrenal failure ACTH levels are inappropriately low. Administration of exogenous glucocorticoid or excessive secretion of endogenous glucocorticoid as in Cushing's syndrome results in suppression of the hypothalamo-pituitary adrenal (HPA) axis and occurs at all levels from the hypothalamus, pituitary and adrenal. This is referred to as tertiary adrenal insufficiency. This means that after excessive glucocorticoid exposure patients will have low cortisol levels and suffer from either a temporary or occasionally permanent cortisol deficiency (tertiary adrenal insufficiency) which results in fatigue, weight loss and a predisposition to an adrenal crisis.

Long acting potent synthetic glucocorticoids such prednisolone and dexamethasone are more likely to cause adrenal suppression than hydrocortisone. Hydrocortisone has the advantage of a short half-life (ca. 3 hours), is the native glucocorticoid, and can be given in low dose. However, current preparations of hydrocortisone cannot reproduce physiological rhythms of cortisol. To maximise the recovery of the HPA the glucocorticoid dose should not exceed the normal daily requirement and also allow initiation of the normal cortisol rhythm. If an immediate release glucocorticoid is given at night then it will generally prevent the night-time activation of the HPA axis. Suppression of the HPA axis may occur due to excessive treatment with exogenous glucocorticoids as in the treatment of inflammatory disorders such as rheumatoid arthritis and asthma. Similarly it is well recognised that Cushing's syndrome either due to a pituitary or ectopic tumour producing ACTH or an adrenal tumour producing cortisol can result in adrenal suppression.

Inflammation is a complex reaction of the body responding to damage of its cells and vascularised tissues. Inflammation can be acute or chronic. An acute inflammatory response is an immediate response by the immune system to a harmful agent. The response includes vascular dilatation, endothelial and neutrophil cell activation. An acute inflammatory response will either resolve or develop into chronic inflammation. Chronic inflammation is an inflammatory response of prolonged duration, weeks, months, or even indefinitely, whose extended time course is provoked by the persistence of the causative stimulus to inflammation within the tissue. The inflammatory process inevitably causes tissue damage. The exact nature, extent and time course of chronic inflammation is variable, and depends on a balance between the causative agent and the attempts of the body to remove it. Aetiological agents producing chronic inflammation include, but are not limited to: infectious organisms that can avoid or resist host defences and so persist in the tissue for a prolonged period; infectious organisms that are not innately resistant but persist in damaged regions where they are protected from host defences; irritant non-living foreign material that cannot be removed by enzymatic breakdown or phagocytosis; or where the stimuli is a "normal" tissue component, causing an auto-immune disease.

Glucocorticoids are commonly used for the treatment of inflammatory diseases. A common side-effect is suppression of the endogenous circadian rhythm of cortisol. The consequence is that patients may need weaning during withdrawal from glucocorticoids and during this weaning period they may have a flare of their disease or suffer from temporary cortisol deficiency that may provoke a flare in their disease. Suppression results from the provision of exogenous glucocorticoid that acts to suppress the circadian rhythm of cortisol. This suppression takes place at all levels of the hypothalamo-pituitary-adrenal axis. An alternative treatment regimen is the use of steroids to treat the inflammatory condition. A steroid such as prednisolone is used to treat rheumatoid arthritis and is effective at reducing inflammation. If steroids are used for extended periods their side effects include osteoporosis, thinning of skin, weight gain and muscle wasting all features of Cushing's syndrome. In addition the administration of steroids suppresses the endogenous circadian secretion of cortisol by the adrenal glands and this has consequences for the patient who is treated with the steroid.

It is well recognised that depression is associated with loss of the normal cortisol circadian rhythm. Similarly it is well recognised that Cushing's syndrome where a tumour results in loss of the circadian rhythm of cortisol causes depression [e.g. loss of circadian rhythm causes disease]. Conditions which result in depression or a general malaise are well known. These include, but are not limited to, clinical depression, reactive depression, post-natal depression, depression which results as a consequence of extensive surgery, chronic fatigue, myalgic encephalitis and conditions such as jetlag. Depressive conditions can also be induced by external effects which are self imposed, for example depression can result when a person is either dieting in an effort to lose weight or also when a person is attempting to treat an addiction, for example smoking or cocaine addiction. There are also less serious conditions which result in general malaise, for example shift workers who work unsociable hours can become tired and depressed due to disruption in their normal sleep pattern. It is also known that certain periods of the year induce depression, for example Christmas and Seasonal Affective Disorder (SAD). The physiological effects of depression are varied. However, some general characteristics include, hyperactivity of the hypothalamo-pituitary-adrenal axis resulting in high cortisol levels, loss of the cortisol circadian rhythm and sleep disturbance with early morning waking. High glucocorticoid levels at night-time or at the time of going to sleep may also themselves disturb sleep.

In WO2003/015793 and WO2010/032006 we disclose pharmaceutical delayed and sustained formulations that deliver glucocorticoids in a delayed and sustained fashion in the control of adrenal insufficiency and other conditions. This disclosure relates to the use of delayed release formulations which surprisingly can also be used in the treatment of conditions that would benefit from the circadian delivery of glucocorticoids such as hydrocortisone such as primary, secondary and tertiary adrenal insufficiency, inflammatory disease and conditions and depression and depressive illnesses

STATEMENTS OF INVENTION

According to an aspect of the invention there is provided a pharmaceutical composition adapted for oral administration comprising: a core comprising hydrocortisone and a carrier and contacting said core a layer comprising a delayed release polymer wherein said delayed release polymer is a pH sensitive enteric polymer and is adapted to delay release of hydrocortisone from said core.

According to an aspect of the invention there is provided a pharmaceutical composition adapted for oral administration comprising: a core comprising hydrocortisone and a carrier and contacting said core a layer comprising a delayed release polymer wherein said delayed release polymer is a single or blend of pH sensitive enteric polymer(s) and is adapted to delay release of hydrocortisone from said core characterized in that the core comprises microcrystalline cellulose which is 75-85% w/w of the composition.

Thus for a medication to replicate this rhythm, when taken last thing at night between approximately 20:00 to 24:00 h, the medication would require a delay in release of 2 to 5 hours and a release to provide a peak level between 06:00 to 09:00 h and maintain cortisol levels above 100 nmol/l until approximately 19:00 h. Naturally this medication could be taken earlier in the evening or later depending on the subjects normal sleep pattern and the rhythm would then be appropriately phase advanced or delayed.

In a preferred embodiment of the invention said carrier is a hydrophilic molecule.

In a preferred embodiment of the invention said hydrophilic molecule or polymer is selected from the group consisting of: mannitol, xylitol, sucrose or glucose.

Preferably said hydrophilic molecule is in the form of a sugar bead.

In an alternative preferred embodiment of the invention said carrier is a hydrophilic polymer.

In a preferred embodiment of the invention said hydrophilic polymer is hydroxypropylmethylcellulose or hydroxypropylethylcellulose.

In an alternative preferred embodiment of the invention said carrier is a hydrophobic polymer or small molecule.

Preferably said hydrophobic polymer is microcrystalline cellulose or dicalcium phosphate.

In a preferred embodiment of the invention said carrier comprises microcrystalline cellulose particles wherein the diameter of said particles is between 200 µm to 1200 µm.

Preferably the diameter of said particles is 500 µm to 800 µm.

In a preferred embodiment of the invention said carrier comprises or consists essentially of 75-85% w/w microcrystalline cellulose of the composition.

Preferably said carrier comprises 80-82% w/w microcrystalline cellulose; most preferably about 81% w/w microcrystalline cellulose of the composition.

In a preferred embodiment of the invention hydrocortisone is present in or on the said carrier between a concentration of 2-10% w/w of the composition.

More preferably the concentration of hydrocortisone in or on the said carrier is between a concentration of 5-8% w/w of the composition.

In a preferred embodiment of the invention the concentration of hydrocortisone is about 6% w/w of the composition.

In a preferred embodiment of the invention hydrocortisone is present in or on the said carrier together with a binding agent such as povidone.

Preferably the concentration of povidone is between the concentration 0.5-4% w/w of the composition.

More preferably the concentration of povidone is between the concentration 1.5-3% w/w of the composition.

In a preferred embodiment of the invention povidone is provided at a concentration of about 1.8% w/w of the composition.

In a preferred embodiment of the invention said delayed release layer is an enteric polymer wherein the dissolution of said composition is between pH 5.5 and 7.0; preferably between pH 6.0 and 6.8.

In a preferred embodiment of the invention said enteric polymer is selected from the group consisting of: acrylic and/or poly [methyl] acrylic polymers, cellulose acetate succinate or polyvinylacetate phathlate.

Preferably, said enteric polymer is a methacrylic acid derivative; preferably Eudragit L100 and/or Eudragit S100.

In a preferred embodiment of the invention said enteric polymer is Eudragit S100.

In an alternative preferred embodiment of the invention said layer consists essentially of a mixture of Eudragit S100 and Eudragit L100.

In a preferred embodiment of the invention the ratio of Eudragit S100 and Eudragit L100 is about 4:1.

In a preferred embodiment of the invention said enteric polymer is provided at between 5-10% w/w; preferably 6-8% w/w, most preferably about 7% w/w of the composition.

In a preferred embodiment of the invention said enteric polymer layer comprises a plasticiser such as dibutyl sebacate.

Preferably the dibutyl sebacate in said enteric polymer layer is present between 0.5-1.0% w/w of the composition.

More preferably the dibutyl sebacate in said enteric polymer layer is present at about 0.7% w/w of the composition.

According to an aspect of the invention there is provided a pharmaceutical composition adapted for oral administration comprising:
a core comprising hydrocortisone and a carrier;
a layer comprising a delayed release polymer contacting said core wherein said delayed release polymer is a pH sensitive enteric polymer which is a mixture of Eudragit L100 and Eudragit S100 [1:4] at about 6-7% w/w of the composition, which is adapted to delay release of hydrocortisone from said core.

In a preferred embodiment of the invention said composition consists essentially of a core and delayed release layer as represented in Table 1.

In a preferred embodiment of the invention said composition comprises 1-30 mg per unit dose of hydrocortisone or cortisone acetate; preferably about 5, 10, 20, or 30 mg of hydrocortisone per unit dose.

In a preferred embodiment of the invention said composition is compressed into a tablet or filled into an outer capsule or moulded into an appropriate dosage form which can administered orally.

When administered the hydrocortisone preparation is administered in pharmaceutically acceptable preparations. Such preparations may routinely contain pharmaceutically acceptable diluents, carriers or processing aids such as inorganic salts, excipient fillers, buffering agents, preservatives and compatible carriers.

Such amounts will depend, of course, on the particular condition being treated, the severity of the condition, the individual patient parameters including age, physical condition, size and weight, the duration of the treatment, the nature of concurrent therapy (if any), and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. The hydrocortisone preparation used contains an effective amount of drug for producing the desired response in a unit of weight or volume suitable for administration to a patient.

The doses of hydrocortisone administered to a subject can be chosen in accordance with different parameters, in particular the state of the subject and also their weight. Other factors include the desired period of treatment. In the event that a response in a subject is insufficient at the initial doses applied, higher doses (or effectively higher doses by a different, more localized delivery route) may be employed to the extent that patient tolerance permits.

Administration of hydrocortisone preparations to mammals other than humans, (e.g. for testing purposes or veterinary therapeutic purposes), is carried out under substantially the same conditions as described above although dosages will vary in accordance with the size of the animal treated. A subject, as used herein, is a mammal, preferably a human, and including a non-human primate, cow, horse, pig, sheep, goat, dog, cat or rodent.

When administered, the hydrocortisone preparation is administered in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Hydrocortisone preparations may be combined, if desired, with a pharmaceutically-acceptable carrier. The term "pharmaceutically-acceptable carrier" as used herein means one or more compatible solid or liquid fillers, diluents or encapsulating substances which are suitable for administration into a human and are typically inert. The term "carrier" denotes an organic or inorganic ingredient, natural or synthetic, with which the active ingredient is combined to facilitate the application. The components of the pharmaceutical compositions also are capable of being co-mingled with hydrocortisone, and with each other, in a manner such that there is no interaction which would substantially impair the desired pharmaceutical efficacy.

The multi-particulate core matrix is combined with pharmaceutically acceptable excipients, which may include: (a) fillers such as lactose, manitose, dicalcium phosphate, microcrystalline cellulose, starch, pre-gelatanised starch, (b) binders such as hydroxypropyl cellulose, polyvinyl pyrrolidone, polyvinyl acetate, (c) powder flow enhancers such colloidal silicon dioxide (d) lubricants such as magnesium stearate, sodium stearyl fumarate (e) disintegrants such as sodium starch glycollate and polyvinyl pyrrolidone and (f) anti-sticking agents such as talc.

The hydrocortisone preparation may contain suitable solubility enhancing and buffering agents. The hydrocortisone preparation also may contain, optionally, compatible preservatives or chemical and physical stabilising agents known to those skilled in the art.

In an alternative preferred embodiment of the invention hydrocortisone may be substituted for cortisone acetate.

According to a further aspect of the invention there is provided a pharmaceutical composition according to the invention for use in the treatment of adrenal dysfunction.

Preferably the adrenal dysfunction is caused by a condition selected from the group consisting of: primary or secondary or tertiary adrenal failure, congenital adrenal hyperplasia, late-onset congenital adrenal hyperplasia, polycystic ovarian failure, glucocorticoid-remediable aldosteronism (GRA).

In a preferred embodiment of the invention said condition is tertiary adrenal insufficiency.

Tertiary adrenal insufficiency is adrenal insufficiency as a result of previous steroid treatment or Cushing's syndrome. For tertiary adrenal insufficiency the treatment regimen can be for traditional adrenal insufficiency but at the same time there may be a desire to wean the subject off steroids and attempt a recovery of the pituitary adrenal access e.g. steroid withdrawal. In this situation the treatment regimen would be to give a delayed formulation according to the invention at night to reproduce the overnight secretion of cortisol and gradually wean down the dose to allow recovery of the pituitary adrenal access. This type of regimen could be applied to different indications for example patients who had high dose steroids for some time for inflammatory disease such as rheumatoid arthritis or in cancer therapy. Typically, the treatment regimen would allow recovery from tertiary adrenal insufficiency or partial suppression of the pituitary adrenal access.

In a preferred embodiment of the invention adrenal dysfunction is caused by congenital adrenal dysfunction.

In a preferred embodiment of the invention said composition is administered at between 20:00 hrs and 24:00 hrs; preferably a second composition is administered between 06:00 hr and 10:00 h.

According to an aspect of the invention there is provided a method to treat adrenal insufficiency in a subject that is deficient in adrenal cortisol secretion or has glucocorticoid-remediable aldosteronism (GRA), said method comprising or consisting of:
  i) administering a first composition according to the invention between 20:00 h and 24:00 h; and
  ii) administering a second composition according to the invention between 06:00 h and 10:00 h wherein the combination of first and second compositions reproduce the normal circadian rhythm of cortisol secretion thereby controlling adrenal insufficiency in a physiological manner.

According to a further aspect of the invention there is provided a treatment regimen to treat adrenal insufficiency or glucocorticoid-remedial aldosteronism comprising or consisting of providing a first composition according to the invention to a subject that is suffering from adrenal insufficiency and administering said first composition at between 20:00 h and 24:00 h; and providing a second composition according to the invention and administering to said same subject between 06:00 h and 10:00 h for use in the control of adrenal insufficiency.

In a preferred method or use of the invention said first and second compositions comprise 1-60 mg of hydrocortisone; preferably about 5-40 mg of hydrocortisone; preferably given two thirds at night and one third in the morning for example 50-70% in the evening and 30-50% in the morning.

In a preferred method or use of the invention adrenal insufficiency is caused by a condition selected from the group consisting of: primary or secondary or tertiary adrenal failure, congenital adrenal hyperplasia, late-onset congenital adrenal hyperplasia, polycystic ovarian failure or Addison's disease.

According to a further aspect of the invention there is provided a pharmaceutical composition according to the invention for use in the treatment of inflammatory diseases or conditions.

Preferably the inflammatory disease or condition is the result of an autoimmune disease.

There is a vast array of diseases exhibiting a chronic inflammatory component. These include but are not limited to: inflammatory joint diseases (e.g., rheumatoid arthritis, polymyalgia rheumatica (PMR) osteoarthritis, polyarthritis and gout), chronic inflammatory connective tissue diseases (e.g., systemic lupus erythematosus, scleroderma, Sjorgen's syndrome, poly- and dermatomyositis, vasculitis, mixed connective tissue disease (MCTD), tendonitis, synovitis, bacterial endocarditis, osteomyelitis and psoriasis); chronic inflammatory lung diseases (e.g., asthma, chronic respiratory disease, pneumonia, fibrosing alveolitis, chronic bronchitis, chronic obstructive pulmonary disease (COPD), bronchiectasis, emphysema, silicosis and other pneumoconiosis and tuberculosis); chronic inflammatory bowel and gastro-intestinal tract inflammatory diseases (e.g., ulcerative colitis and Crohn's disease); chronic neural inflammatory diseases (e.g., chronic inflammatory demyelinating polyradiculoneuropathy, chronic inflammatory demyelinating polyneuropathy, multiple sclerosis, Guillan-Barre Syndrome and myasthemia gravis); other inflammatory diseases (e.g., mastitis, laminitis, laryngitis, chronic cholecystitis, Hashimoto's thyroiditis, inflammatory breast disease); chronic inflammation caused by an implanted foreign body in a wound; and including chronic inflammatory renal diseases including crescentic glomerulonephritis, lupus nephritis, ANCA-associated glomerulonephritis, focal and segmental necrotizing glomerulonephritis, IgA nephropathy, membranoproliferative glomerulonephritis, cryoglobulinaemia and tubulointerstitial nephritis. Diabetic nephropathy may also have a chronic inflammatory component and chronic inflammatory responses are involved in the rejection of transplanted organs. It is apparent that many diseases have an inflammatory component many of which are autoimmune diseases.

In a preferred embodiment of the invention said inflammatory disease is rheumatoid arthritis or polymyalgia rheumatica.

In an alternative embodiment of the invention said inflammatory disease is inflammatory bowel disease.

In a preferred embodiment of the invention said inflammatory bowel disease is selected from the group consisting of: Crohn's disease, ulcerative colitis, collagenous colitis, lymphocytic colitis, ischaemic colitis, diversion colitis, Behcet's colitis.

In a preferred embodiment of the invention said inflammatory bowel disease is Crohn's disease.

In a further preferred embodiment of the invention said inflammatory bowel disease is ulcerative colitis.

In a preferred embodiment of the invention said composition is administered before sleep, for example between 20:00 hrs and 24:00 hrs.

According to an aspect of the invention there is provided a method to treat an inflammatory disease or condition in a subject that is suffering from said disease or condition, comprising or consisting of administering an effective amount of at least one composition according to the invention prior to sleep wherein said composition[s] does not suppress the normal circadian rhythm of cortisol secretion and controls said inflammatory disease or condition.

In a preferred method of the invention said disease is rheumatoid arthritis.

In an alternative preferred method of the invention said disease is inflammatory bowel disease.

Preferably inflammatory bowel disease is Crohn's disease or ulcerative colitis.

In a preferred method or use of the invention said first and second compositions comprise 1-60 mg of hydrocortisone; preferably about 5-40 mg of hydrocortisone; most preferably 20-30 mg of hydrocortisone.

In a preferred method of the invention said composition according to the invention is provided once nightly.

According to a further aspect of the invention there is provided a pharmaceutical composition according to the invention wherein said composition provides a delayed release of hydrocortisone to reset and re-entrain the circadian rhythm of cortisol in the treatment of depression or depression associated conditions.

Diseases or conditions that would benefit from entrainment of cortisol secretion include but are not limited to, depression, sleep disorder, fatigue, abnormal eating, addiction, anxiety, immune response, inflammation, arthritis, asthma, jet lag.

In a preferred embodiment of the invention said use is the treatment of depression or a condition which results in depression, or similar condition.

In a preferred embodiment of the invention the depression is clinical depression.

In a further preferred embodiment of the invention the depression is reactive depression.

In a still further preferred embodiment of the invention the depression is post-natal depression.

In a further preferred embodiment of the invention said condition or malaise is selected from the following group: chronic fatigue syndrome; myalgic encephalitis; jet lag; shift work, depression resulting from a person being overweight; depression resulting from dieting; depression resulting from the treatment of cigarette addiction; depression resulting from the treatment of alcohol addiction; depression resulting from the treatment of drug addiction (e.g. cocaine, heroin); the treatment of seasonal affective disorder or a like condition.

In a further preferred embodiment of the invention said condition results from the administration of an antipsycotic drug.

In a preferred method of the invention said antipsycotic drug is selected from the group consisting of: clozapine, olanzapine, risperidone, quetiapine or sertindole.

According to a further aspect of the invention there is provided a process for the manufacture of a delayed release hydrocortisone formulation comprising the following steps:
i) forming a suspension comprising hydrocortisone and a binding agent in an aqueous vehicle;
ii) providing a micro-particulate carrier;
iii) applying the hydrocortisone suspension to the micro-particulate carrier to coat said carrier;
iv) drying the hydrocortisone coated micro-particulate carrier;
v) providing a colloidal solution comprising a delayed release polymer wherein said delayed release polymer is a single or blend of pH sensitive enteric polymer(s), a solvent or mixture of solvents, an anti-tacking/flow agent and a plasticizer;
vi) applying the solution formed in (v) to the dried micro-particulate carrier in vii); and optionally
viii) encapsulating the finished formulation in unit dosage form.

In a preferred process of the invention the binding agent includes providone.

In a preferred process of the invention the micro-particulate carrier is micro-crystalline cellulose or sugar beads.

In preferred process of the invention said blend of delayed release polymers comprises a mixture of Eudragit S100 and Eudragit L100.

Preferably the blend of Eudragit S100 and Eudragit L100 is in a ratio of about 4:1.

In a preferred process of the invention said plasticiser is dibutyl sebacate.

In a preferred process of the invention said anti-tacking/flow agent is talc.

In a preferred method of the invention hydrocortisone and the binding agent solution is applied as a spray.

In a preferred method of the invention process the delayed release polymer solution is applied as a spray.

According to a further aspect of the invention there is provided a pharmaceutical formulation manufactured by a process according to the invention.

In a preferred embodiment of the invention hydrocortisone is provided at a final concentration of between 2-10% w/w or 5-8% w/w or about 6% w/w of the composition formed by the process.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures.

DEFINITIONS

Figure 1:
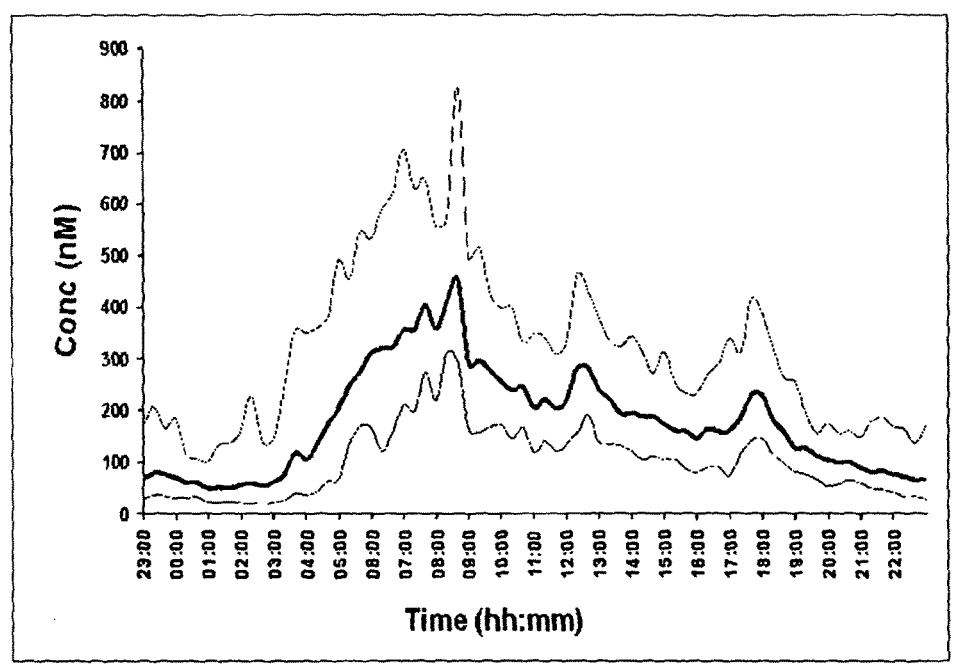
FIG. 1: illustrates the analysis of 24 hours circadian profile in healthy volunteers.

"Controlled release" is the drug release profile delivered by a dosage form, usually via zero-order or first order, with the objective of maintaining a level of drug in the bloodstream which is invariant with time over the dosing interval.

"Delayed release" is the drug release profile delivered by a dosage form which is characterised by an initial period of complete absence of drug release or very low drug release, typically less than or equal to 10% of the overall dose in the dosage form, prior to the main drug release phase.

"Sustained release" is the drug release profile delivered by a dosage form, usually via first order or pseudo first order, with the objective of sustaining the duration of release such that the frequency of dosing is less than or equal to half that achieved with an immediate release dosage form.

"Enteric polymer" is a homopolymer or copolymer or mixtures thereof that have pH dependent solubility in aqueous media characterised generally by low aqueous solubility under acidic conditions (pH1-4) and higher aqueous solubility under weakly acidic conditions and above (pH>5). The purpose is to protect the dosage from polymer dissolution mediated release in the acidic gastric environment of the gut.

"Eudragit L100" is a defined mixture of polymethacrylates [CAS number: 2506-15-1] with the chemical composition: poly(methacrylic acid, methyl methacrylate) in a ratio of 1:1.

"Eudragit S100" is a defined mixture of polymethacrylates [CAS number: 25086-15-1] with the chemical composition: poly(methacrylic acid, methyl methacrylate) in a ratio of 1:2.

The terms "multi-particulate" and "micro-particulate" are to be used interchangeably and are equivalent to one another in form and function.

Materials and Methods

Method of Manufacture

The manufacturing process for Formulation DIURF-001 involves steps 1-4

The manufacturing process for Formulation DIURF-006 involves steps 1, 3 and 4 only.

Process Step 1: Description of the Preparation of the Hydrocortisone Coated Cellets®

Weigh out the required materials in the relevant quantities.

Add the Povidone to the water and mix using an overhead stirrer for approximately 5 minutes.

To the Povidone solution add the hydrocortisone and homogenise using an appropriate homogeneiser. Mix until homogenous (approximately 30 minutes).

Remove the homogeniser and replace with an overhead stirrer. Ensure the suspension is mixed throughout the spray process.

Set up the Fluid Bed Drier (example: Glatt GPCG3) with the Wurster attachment and retaining basket.

Place the Cellets® into the Fluid Bed Drier and fluidise until a product temperature of above 20° C. is reached.

Set the Wurster attachment to 25 mm height whilst the Cellets® are fluidised.

Spray on the API solution using the following parameters:—
Atomising air=~1.8 bar
Filter Shaker=15 seconds every 30 seconds
Inlet air temperature=40° C.
Inlet air volume=60 m$^3$/sec
Pump Speed=~15 g/min (for first 30 minutes), ~18 g/min thereafter.
[Use: 400 μm retaining basket for the above operation]

Determine the end-point by the amount of suspension sprayed onto the batch by weight.

After the spraying process has finished the hydrocortisone coated Cellets® are kept fluidised for 30 minutes to allow them to dry sufficiently.

Sieve the hydrocortisone coated Cellets® through a 1.4 mm sieve, this will remove any agglomerates.

Process Step 2: Description of the Sustained Release Coating

Weigh out the required materials in the relevant quantities.

Mix together the isopropanol, acetone, Eudragit RL100/RS100 using an overhead stirrer at a speed enough to create a vortex but without overspill. Mix until a solution is obtained.

Add the dibutyl sebacate, purified water and talc to the solution and continue mixing throughout the coating process to keep the talc suspended.

Set up the Fluid Bed Drier with Wurster attachment and retaining basket.

Place the hydrocortisone coated Cellets® (from Unit process 1) into the Fluid Bed Drier and fluidise until a product temperature of between 20° C. and 25° C. is reached.

Set the Wurster attachment to 25 mm height whilst the hydrocortisone coated Cellets® are fluidised.

Spray on the polymer suspension using the following parameters:—
Atomising air=~1.8 bar
Filter Shaker=15 seconds every 30 seconds
Inlet air temperature=25° C.
Inlet air volume=60 m$^3$/sec
Pump Speed=~15 g/min (for first 30 minutes), ~18 g/min thereafter.
[Use: 400 μm retaining basket for the above operation]

Determine the end-point by the amount of suspension sprayed onto the batch by weight.

Once the end point has been reached stop spraying the suspension and remove the hydrocortisone sustained release coated Cellets® from the Fluid Bed Drier.

Sieve the hydrocortisone sustained release coated Cellets® through a 1.4 mm sieve, this will remove any agglomerates.

Add approximately 1% weight of talc to the hydrocortisone sustained release coated Cellets® to reduce the possibility of any sticking.

Process Step 3: Description of the Enteric (Delayed Release) Coating

Weigh out the required materials in the relevant quantities.

Mix together the isopropanol, acetone, Eudragit S100 and L100 using an overhead stirrer at a speed enough to create a vortex but without overspill. Mix until a solution is obtained.

Add the dibutyl sebacate, water and talc to the solution and continue mixing throughout the coating process to keep the talc suspended.

Set up the Fluid Bed Drier with Wurster attachment and retaining basket.

Place the hydrocortisone sustained release coated Cellets® into the Fluid Bed Drier and fluidise until a product temperature of between 20° C. and 25° C. is reached.

Set the Wurster attachment to 25 mm height whilst the hydrocortisone sustained release coated Cellets® are fluidised.

Spray on the polymer suspension using the following parameters:—
Atomising air=~1.8 bar
Filter Shaker=15 seconds every 30 seconds
Inlet air temperature=25° C.
Inlet air volume=60 m$^3$/sec
Pump Speed=~15 g/min (for first 30 minutes), ~18 g/min thereafter.
[Use: 400 μm retaining basket for the above operation]

Determine the end-point by the amount of suspension sprayed onto the batch by weight.

Once the end point has been reached stop spraying the suspension and remove the Hydrocortisone sustained and delayed release coated Cellets® from the Fluid Bed Drier.

Sieve the hydrocortisone delayed and sustained release coated Cellets® through a 1.4 mm sieve, this will remove any agglomerates.

Add approximately 1% weight of talc to the hydrocortisone delayed and sustained release coated Cellets® to reduce the possibility of any sticking.

Process Step 4: Description of the Encapsulation, Bulk Packaging and Labelling

Set up the encapsulation machine.

Fill hopper with the hydrocortisone delayed and sustained release coated Cellets® (from Unit process 3).

Fill capsule holder with the empty size 00 capsule shells.

Set machine to fill at the required fill weight.

Dissolution Methodology

Dissolution testing of Hydrocortisone Controlled Release multi-particulates was conducted using USP Apparatus I (Baskets), with a total of 900 mL of dissolution media, involving two subsequent sequential media changes, and a basket speed of 100 rpm. Dissolution was conducted initially in 700 mL of simulated gastric fluid (USP, pH 1.2) for 2 hours, followed by further dissolution in 850 mL of media adjusted to pH 6.0 (via the addition of pre-warmed 150 mL of 0.18M trisodium ortho phosphate dodecahydrate buffer) for 1 hour, and then dissolution in 900 mL of media adjusted to pH 7.2 (via the addition of pre-warmed 50 mL of 0.23M trisodium ortho phosphate dodecahydrate buffer).

Assay of Hydrocortisone

The concentration of Hydrocortisone in the multi-particulates and released during the dissolution evaluation was determined using the following method. The hydrocortisone solution was diluted in the mobile phase solution comprising tetrahydrofuran/water (20:80 v/v). The resulting solution was into a HPLC, set-up with a Phenomenex Luna column C18(2), 5 μm, 150 mm×4.6 mm, equilibrated at 45° C. The samples were run using Isocratic conditions employing tetrahydrofuran/water (20:80 v/v) as the mobile phase at a flow rate of 1.5 mL/minute. Detection is by UV at a wavelength of 254 nm.

Example 1

The circadian secretion of cortisol in human subjects was analyzed in healthy volunteers. The measurement of cortisol was by liquid chromatography-mass spectrometry (LC-MS). The geometric mean (black line) of the cortisol levels was calculated; see FIG. 1. The top grey line is the $90^{th}$ centile for geometric mean and the bottom grey line is the 10th centile for the geometric mean. Samples were obtained at 20 min intervals. The 24 h cortisol profiles in 28 healthy volunteers were measured using a Waters Xevo mass spectrometer with Acquity uPLC system (limit of quantitation 0.01 μg/dl or 0.3 nmol/l, and relative standard deviation <15% at low and <10% at medium and high cortisol levels). The circadian rhythm of cortisol secretion is clearly shown with a peak level between 06:00 to 09:00 h with maintenance of cortisol levels above 100 nmol/l until approximately 19:00 h; see FIG. 1.

Example 2

Figure 2A:
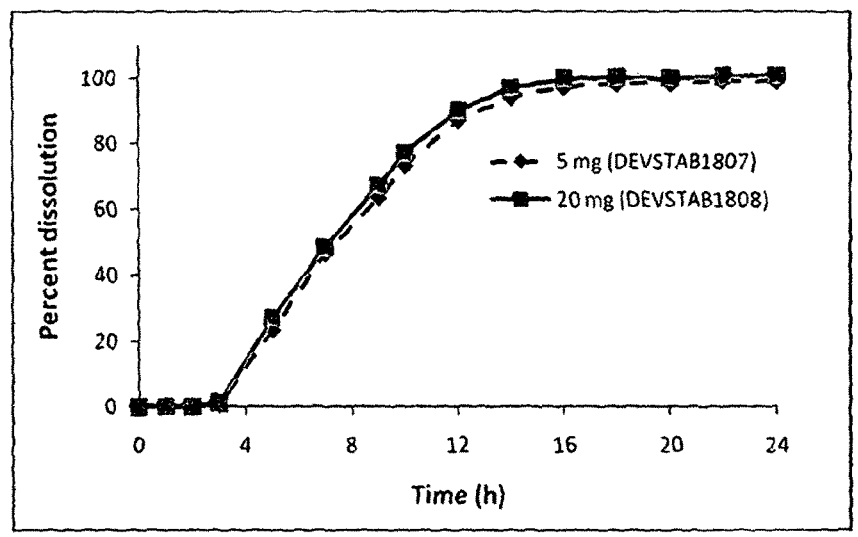
FIG. 2A: illustrates the in vitro dissolution profile of a delayed and sustained release hydrocortisone formulation [DIURF-001] compared to FIG. 2B which illustrates a delayed release hydrocortisone formulation [DIURF-006]
Figure 2B:
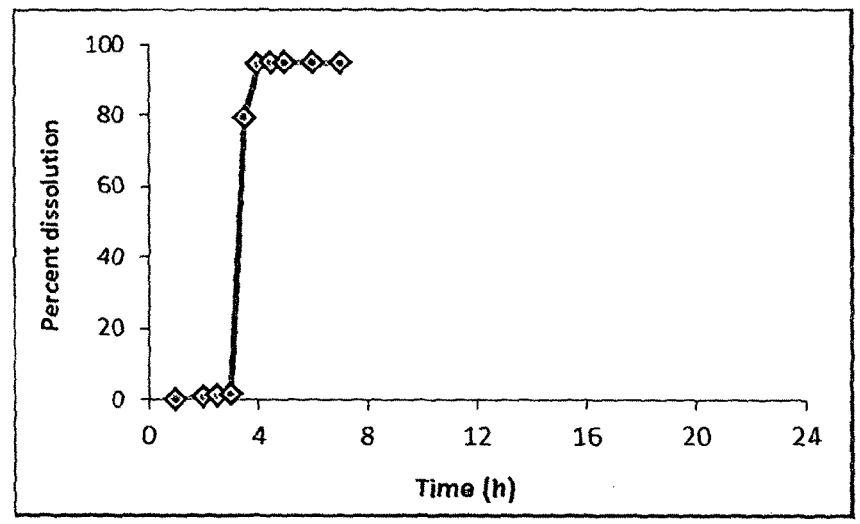

FIG. 2 illustrates the in vitro dissolution of a delayed and sustained release hydrocortisone formulation with a delayed release formulation. FIG. 2A shows an approximate 3-hour delayed period prior to the onset of drug release followed by a sustained drug release phase of c.8-10 hours. In contrast, in FIG. 2B the in vitro dissolution profile of a delayed release hydrocortisone formulation shows a similar 3-hour delayed period prior to the onset of drug release which is followed by an immediate release of hydrocortisone.

Example 3

Figure 3:
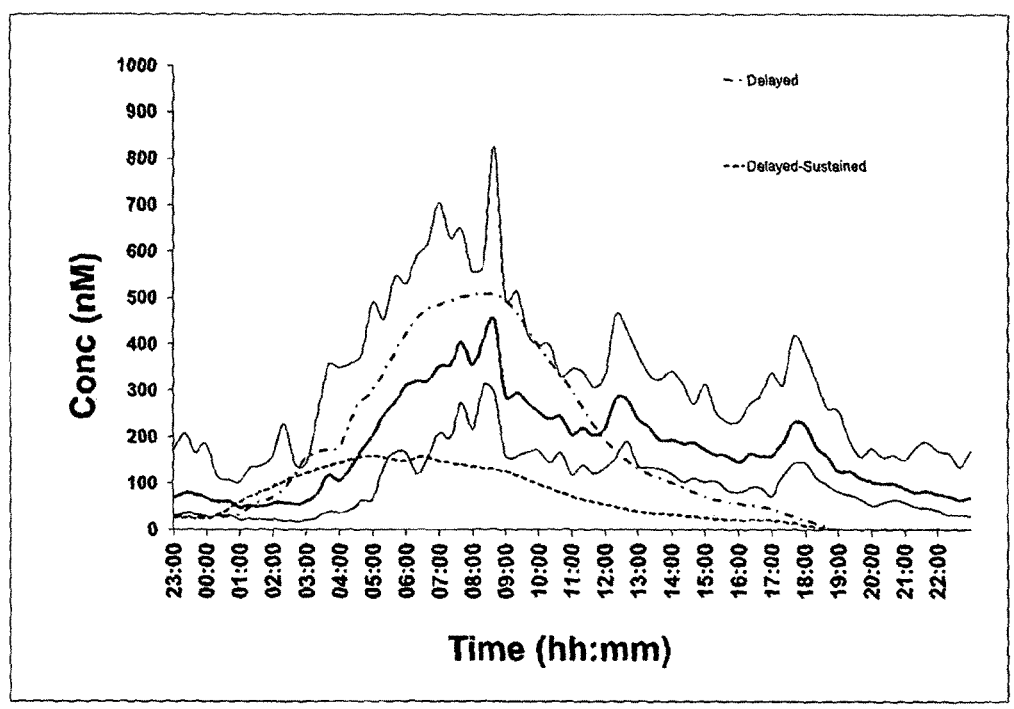
FIG. 3: illustrates a pharmacokinetic comparison of a delayed and sustained release hydrocortisone formulation with a delayed release hydrocortisone formulation.

An in vivo pharmacokinetic comparison in healthy human volunteers (n=6) of 30 mg delayed only hydrocortisone formulation compared to a 30 mg delayed-sustained hydrocortisone formulation is illustrated in FIG. 3. The analysis was conducted by LC-MS and comparison is made to the normal circadian cortisol profile already shown in FIG. 1. The comparison is illustrated below:

Normals:
AUC/Bioavailability=4697 nM·hr
Cmax=451.5 nMol/l
Tmax=07:52 h

Figure 4:
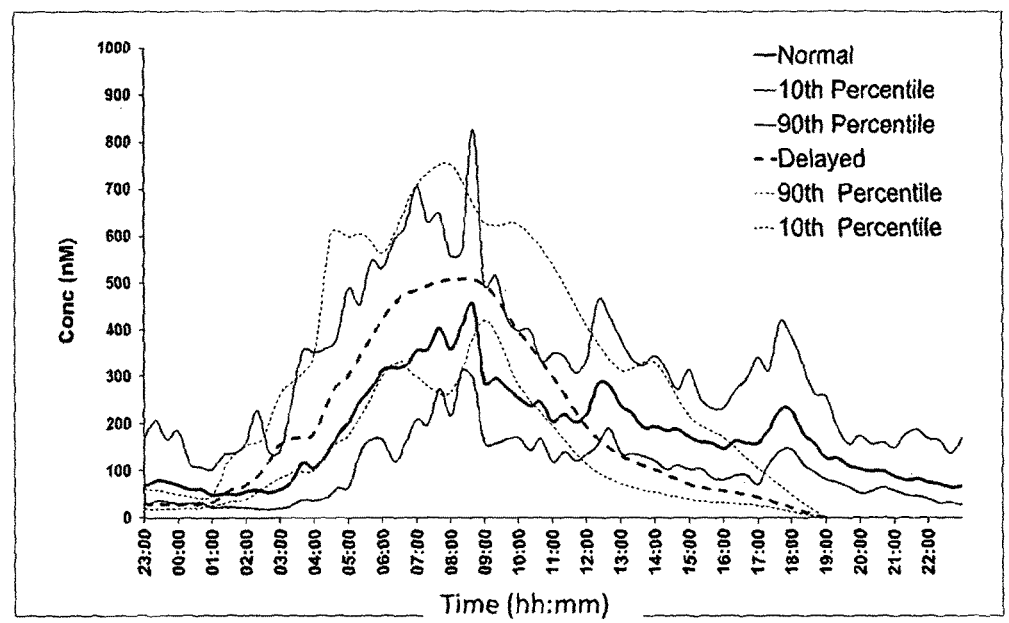
FIG. 4 is a delayed hydrocortisone profile compared to normal circadian profile to illustrate the reproduction of the circadian release of cortsol using a delayed formulation of hydrocortisone.

Delayed Release Formulation:
AUC/Bioavailability of delayed=4595 nm·hr (98% compared to normals)
Cmax=507.0 nMol/l
Tmax=08:00 h Delayed-Sustained Release Formulation:
AUC/Bioavailability=1628 nM·hr (35% compared to Normals)
Cmax=159 nMol/l
Tmax=05:00 h The delayed release hydrocortisone formulation has a greater Cmax, a later Tmax and greater AUC than the delayed and sustained formulation. These results are unexpected based on the in vitro dissolution data shown in FIGS. 2A and 2B and in the prior art which teaches the provision of a delayed and sustained release formulation is required to provide hydrocortisone formulations with the requisite release profile to reproduce the circadian rhythm of cortisol secretion. It would be predicted that a delayed only formulation would generate an earlier Cmax and an un-sustained absorption profile compared to a delayed and sustained formulation. However, in vivo, in humans, the delayed only formulation has a later Tmax, a more sustained absorption and greater AUC than the delayed-sustained formulation and replicates the normal overnight cortisol profile. This is graphically represented in FIG. 4 which shows the geometric mean and $10^{th}$ and $90^{th}$ centile cortisol levels for a 30 mg delayed formulation overlaid on the normal cortisol levels again shown as geometric mean and $10^{th}$ and $90^{th}$ centile.

Example 4

An open label, randomised, single dose, crossover study was conducted in 28 healthy volunteers to characterize the pharmacokinetics of Chronocort® (Formulation DIURF-006) to demonstrate the closeness of fit to the physiological circadian rhythm of cortisol. Healthy volunteers were screened and enrolled onto the study. The principal inclusion criteria were healthy male subjects between the ages of 18 and 60 years, who did not work shifts and who had no clinically significant systemic infections and/or history of allergy/sensitivity to hydrocortisone/dexamethasone. Each subject received Chronocort® (Formulation DIURF-006) on four occasions separated by a one-week washout period. On each occasion the dose of Chronocort® administered was one of the following: 5 mg, 10 mg or 20 mg (given at 23:00 h) or 30 mg (given as 20 mg at 23:00 h and 10 mg at 7:00 h the following day). Prior to each administration of Chronocort® each subject was dosed with dexamethasone (1 mg at approximately 4-6 hourly intervals) to suppress endogenous release of cortisol. Pharmacokinetic sampling was conducted at defined time-points over a course of 24-hour after each Chronocort® dosing.

The plasma concentration of hydrocortisone was determined using a validated high-pressure liquid chromatography mass spectrometry (LC-MS) assay. The analysis of pharmacokinetic parameters was conducted using WinNonlin Professional (version 5.2.1). Comparison of the pharmacokinetic profile for Chronocort® was made in relation to hydrocortisone immediate release tablet (historical in-house data from study DIUR-001) and reference normative cortisol profile of healthy individuals (published by Debono et al., 2009).

Figure 5:
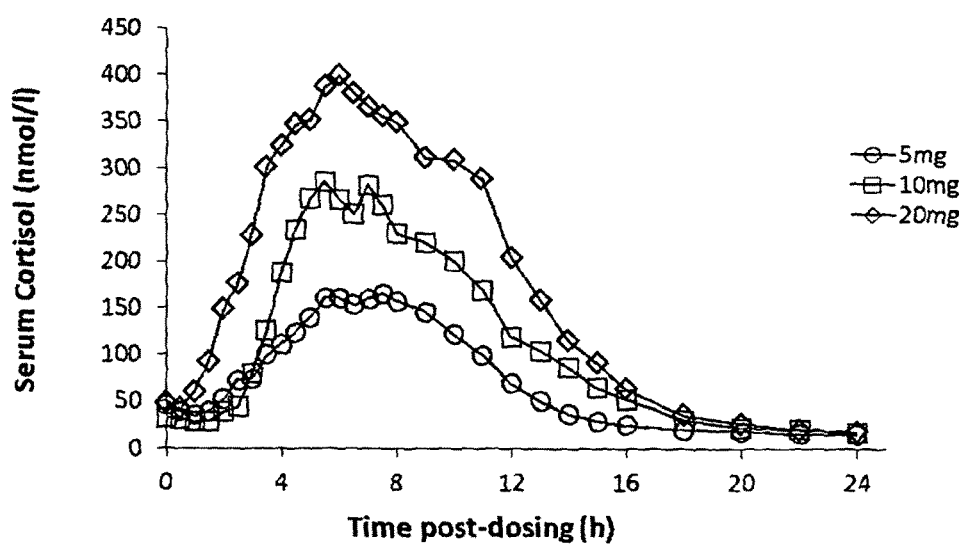
FIG. 5: The mean plasma concentration of hydrocortisone versus time plots for Chronocort® administered in single doses of 5 mg, 10 mg and 20 mg at night (23:00 h)

The pharmacokinetic profiles for Chronocort® administered in single-doses of 5 mg, 10 mg and 20 mg (at 23:00 h) are shown in FIG. 5. All profiles show a characteristic period of delayed release for the initial 2-4 hours post-dosing followed by a gradual rise in plasma concentration attaining a maximal concentration (Cmax) typically around 7-hours post dosing.

Figure 6:
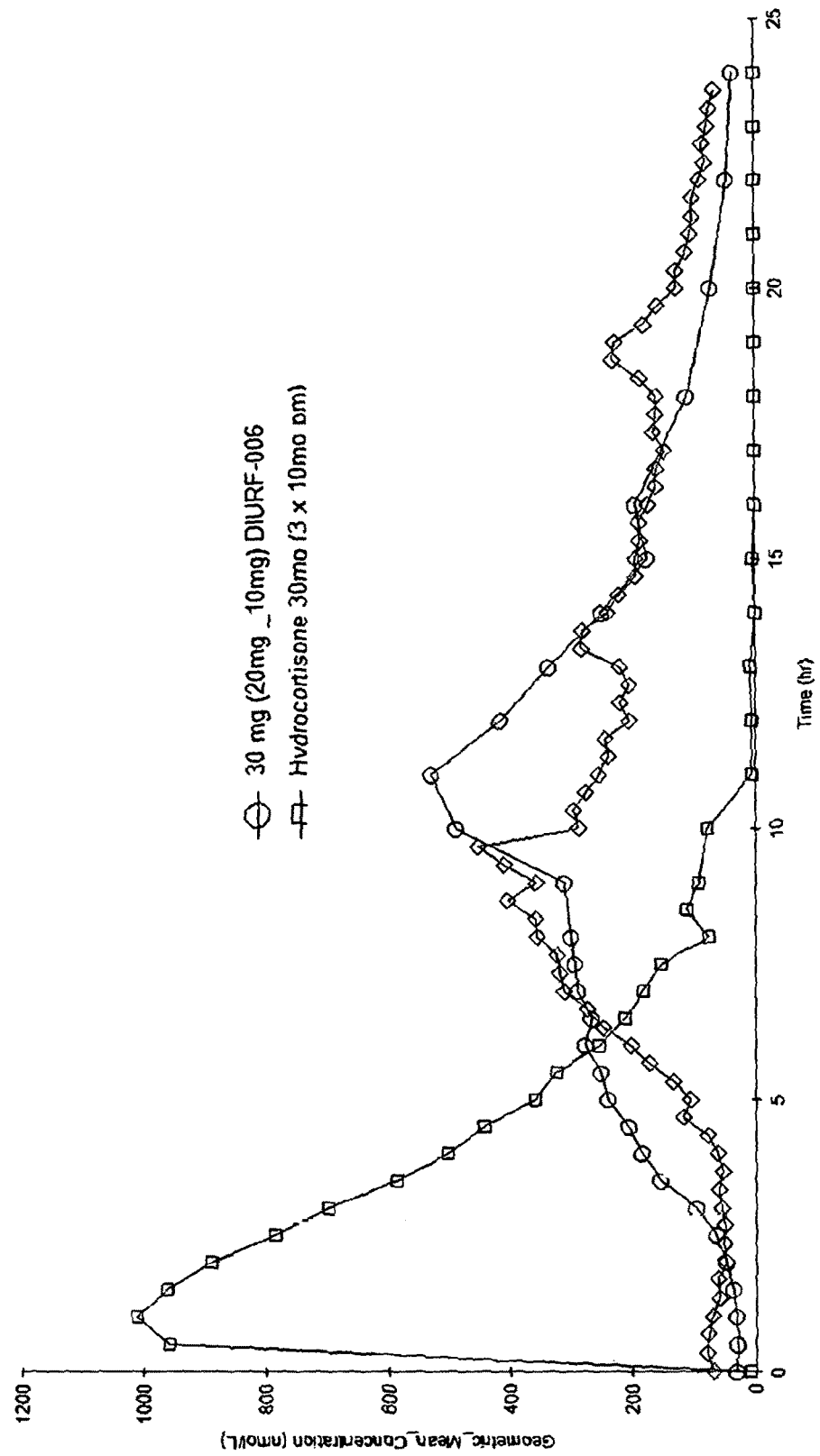
FIG. 6: The mean plasma concentration of hydrocortisone versus time plots for Chronocort® administered in a cumulative dose of 30 mg, given as 20 mg at night (23:00 h) and 10 mg in the morning (7:00 h). Comparison is made to the normative published data for cortisol (Debono et al., 2009) and Hydrocortisone immediate release tablet (from study DIUR-001).

The pharmacokinetic profile for Chronocort® administered in a cumulative dose of 30 mg (20 mg at 23:00 h and 10 mg at 7:00 h) is shown in FIG. 6. The closeness of fit to the normative circadian profile of cortisol in healthy individuals is compared in the same plot. The reference pharmacokinetic profile for hydrocortisone immediate release tablet is also represented to illustrate the marked improvement in the closeness of fit of Chronocort® to the normative cortisol profile in comparison to conventional Hydrocortisone immediate release formulation.

Figure 7:
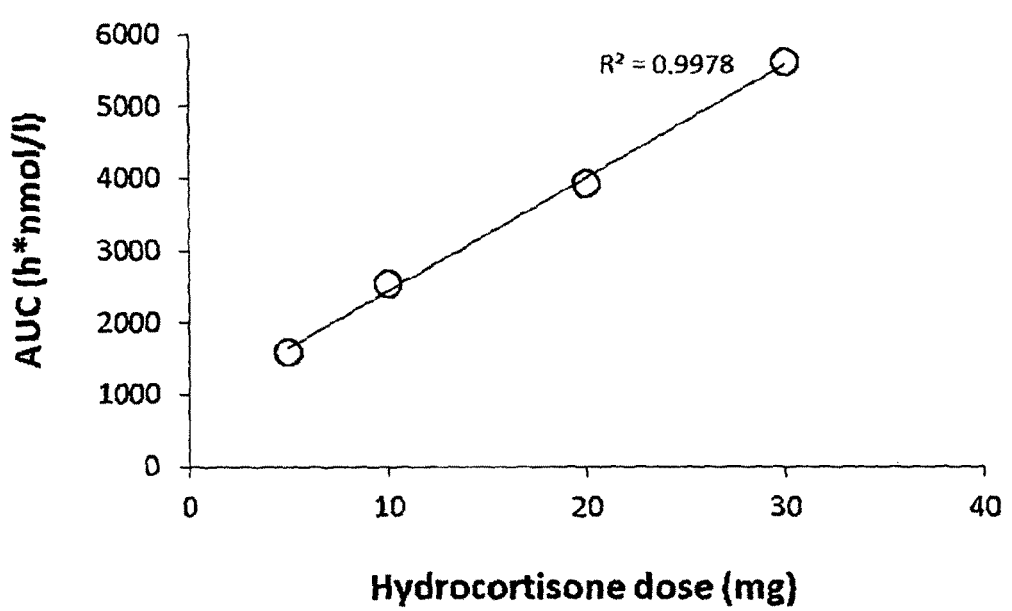
FIG. 7: Comparison of exposure of hydrocortisone from Chronocort® formulation, in respect of area under the curve (AUC0-t) over the dose range 5 mg to 30 mg.

The proportionality of exposure of hydrocortisone from Chronocort® at different doses is shown in FIG. 7. It can be noted that between the dose range of 5 mg to 30 mg, the exposure of hydrocortisone from the Chronocort® formulation is essentially linear.

TABLE 1

Delayed Release Formulation [DIURF-006] Hydrocortisone Modified Release Capsule formulation, dose strengths: 5 mg, 10 mg, 20 mg and 30 mg

| Ingredient | DIURF-006 Grade | Function | Quantity (mg/capsule) 5 mg Capsule | 10 mg Capsule | 20 mg Capsule | 30 mg Capsule | Quantity (% w/w) |
|---|---|---|---|---|---|---|---|
| Microcrystalline cellulose spheres (Cellets ® 500) | Ph. Eur./USP and supplier specification | Inert core | 66.76 | 133.51 | 267.01 | 400.52 | 81.36 |
| Hydrocortisone USP Micronized EP | Ph. Eur./USP | Active agent | 5.00 | 10.00 | 20.00 | 30.00 | 6.09 |
| Water for Injection | Ph. Eur./USP | Coating Solvent | (93.63) | (187.25) | (374.49) | (561.74) | — |
| Povidone (Kollidon 25) | Ph. Eur. | Binder | 1.51 | 3.01 | 6.02 | 9.03 | 1.83 |
| Delayed release coat | | | | | | | |
| Isopropanol Alcohol | BP | Coating Solvent | (46.46) | (92.92) | (185.83) | (278.75) | — |
| Acetone | BP | Coating Solvent | (30.97) | (61.95) | (123.89) | (185.84) | — |
| Water for Injection | Ph. Eur./USP | Coating Solvent | (3.10) | (6.20) | (12.39) | (18.59) | — |
| Eudragit S100 | Ph. Eur./NF | Coating Polymer | 4.40 | 8.81 | 17.61 | 26.42 | 5.37 |
| Eudragit L100 | Ph. Eur./NF | Coating Polymer | 1.10 | 2.20 | 4.40 | 6.60 | 1.34 |
| Talc[1] | BP/NF | Anti-sticking agent | 2.74 | 5.49 | 10.97 | 16.46 | 3.34 |
| Dibutyl Sebacate | NF | Plasticiser | 0.55 | 1.09 | 2.18 | 3.27 | 0.67 |
| Talc[2] | BP/NF | Anti-sticking agent | (0.82) | (1.64) | (3.28) | (4.92) | — |
| Total | | | 82.06 | 164.11 | 328.19 | 492.30 | 100.0 |

( )—Removed during processing, does not appear in the final product, required quantity shown in parenthesis
[1]Talc included in the coating formulation as anti-sticking agent
[2]Talc included extra-granularly as anti-sticking agent and is removed in the manufacturing process

TABLE 2

Delayed and Sustained Release Formulation [DIURF-001] Hydrocortisone Modified Release Capsule formulation, dose strengths: 5 mg, 10 mg and 20 mg

| Ingredient | Grade | Function | Quantity (mg/capsule) 5 mg Capsule | 10 mg Capsule | 20 mg Capsule | Quantity (% w/w) |
|---|---|---|---|---|---|---|
| Microcrystalline cellulose spheres (Cellets ® 500) | Ph. Eur./USP and supplier specification | Inert core | 66.67 | 133.34 | 266.68 | 56.06 |

TABLE 2-continued

Delayed and Sustained Release Formulation [DIURF-001] Hydrocortisone Modified Release Capsule formulation, dose strengths: 5 mg, 10 mg and 20 mg

| Ingredient | Grade | Function | 5 mg Capsule | 10 mg Capsule | 20 mg Capsule | Quantity (% w/w) |
|---|---|---|---|---|---|---|
| Hydrocortisone USP Micronized EP | Ph. Eur./USP | Active agent | 5.00 | 10.00 | 20.00 | 4.20 |
| Water for Injection | Ph. Eur./USP | Coating Solvent | (93.50) | (187.00) | (374.00) | — |
| Povidone (Kollidon 25) | Ph. Eur. | Binder | 1.50 | 3.00 | 6.00 | 1.26 |
| *Sustained release coat* | | | | | | |
| Isopropanol Alcohol | BP | Coating Solvent | (96.03) | (192.06) | (384.12) | — |
| Acetone | BP | Coating Solvent | (64.02) | (128.04) | (256.08) | — |
| Water for Injection | Ph. Eur./USP | Coating Solvent | (6.40) | (12.80) | (25.60) | — |
| Eudragit RS100 | Ph. Eur./NF | Coating Polymer | 4.57 | 9.14 | 18.28 | 3.84 |
| Eudragit RL100 | Ph. Eur./NF | Coating Polymer | 6.86 | 13.72 | 27.44 | 5.77 |
| Talc[1] | BP/NF | Anti-sticking agent | 5.72 | 11.44 | 22.88 | 4.81 |
| Dibutyl Sebacate | NF | Plasticiser | 1.14 | 2.28 | 4.56 | 0.96 |
| Talc[2] | BP/NF | Anti-sticking agent | (1.19) | (2.38) | (4.76) | — |
| *Delayed release coat* | | | | | | |
| Isopropanol Alcohol | BP | Coating Solvent | (102.94) | (205.88) | (411.75) | — |
| Acetone | BP | Coating Solvent | (68.63) | (137.26) | (274.52) | — |
| Water for Injection | Ph. Eur./USP | Coating Solvent | (6.86) | (13.72) | (27.44) | — |
| Eudragit S100 | Ph. Eur./NF | Coating Polymer | 13.73 | 27.46 | 54.92 | 11.55 |
| Eudragit L100 | Ph. Eur./NF | Coating Polymer | 3.43 | 6.86 | 13.72 | 2.88 |
| Talc[1] | BP/NF | Anti-sticking agent | 8.58 | 17.16 | 34.32 | 7.22 |
| Dibutyl Sebacate | NF | Plasticiser | 1.72 | 3.44 | 6.88 | 1.45 |
| Talc[2] | BP/NF | Anti-sticking agent | (1.19) | (2.38) | (4.76) | — |
| | | Total | 118.92 | 237.84 | 475.68 | 100.00 |

( )—Removed during processing, does not appear in the final product, required quantity shown in parenthesis
[1]Talc included in the coating formulation as anti-sticking agent
[2]Talc included extra-granularly as anti-sticking agent and is removed in the manufacturing process

The invention claimed is:

1. An oral pharmaceutical composition, consisting of:
a core comprising hydrocortisone, a binding agent, and a carrier; and
a layer comprising a delayed release polymer, talc, and a plasticizer,
wherein the layer comprising the delayed release polymer is in contact with said core,
wherein said delayed release polymer is a mixture of (i) poly (methacrylic, methyl methyacrylic) in a ratio of 1:1 and (ii) poly (methacrylic, methyl methyacrylic) in a ratio of 1:2, wherein (i) and (ii) are at a ratio of 1:4 and at 6% to 7% w/w of the composition which is adapted to delay release of hydrocortisone from said core,
wherein the hydrocortisone is at a concentration of 5-8% w/w of the composition,
wherein the binding agent comprises povidone at a concentration of 0.5-4.0% w/w of the composition,
wherein the carrier comprises microcrystalline cellulose particles, and wherein the carrier is 75-85% w/w of the composition, and
wherein the plasticizer comprises dibutyl sebacate at 0.5-1.0% w/w of the composition.

2. The composition according to claim 1, wherein said microcrystalline cellulose particles have a diameter of 200 μm to 1200 μm.

3. The composition according to claim 2, wherein the diameter of said microcrystalline cellulose particles is 500 μm to 800 μm.

4. The composition according to claim 1, wherein said composition comprises 80-82% w/w microcrystalline cellulose particles.

5. The composition according to claim 4, wherein said composition comprises 81.36% w/w microcrystalline cellulose particles.

6. The composition according to claim 1, wherein the hydrocortisone is 6.09% w/w of the composition.

7. The composition according to claim 1, wherein the concentration of hydrocortisone is 6% w/w of the composition.

8. The composition according to claim 1, wherein the concentration of povidone is 1.5-3.0% w/w of the composition.

9. The composition according to claim 8, wherein the povidone is at a concentration of 1.83% w/w of the composition.

10. The composition according to claim 1, wherein dissolution of said composition is pH 5.5 to 7.0.

11. The composition according to claim 1, wherein said delayed release polymer is 5-10% w/w of the composition.

12. The composition according to claim 1, wherein said delayed release polymer is 6-8% w/w of the composition.

13. The composition according to claim 1, wherein (i) is 1.34% w/w of the composition and (ii) is 5.37% w/w of the composition.

14. The composition according to claim 1, wherein the dibutyl sebacate is 0.67% w/w of the composition.

15. A pharmaceutical composition, consisting of:
a core comprising hydrocortisone, a binding agent, and a carrier; and
a layer comprising a delayed release polymer, talc, and a plasticizer,
wherein the layer comprising a delayed release polymer is in contact with said core, wherein said delayed release polymer is a pH sensitive enteric polymer, wherein the pH sensitive enteric polymer is a mixture of (i) poly (methacrylic acid, methyl methacrylate) in a ratio of 1:1 and (ii) poly (methacrylic acid, methyl methacrylate) in a ratio of 1:2, wherein (i) is 1.34% w/w of the composition and (ii) is 5.37% w/w of the composition, wherein the hydrocortisone is 6.09% w/w of the composition, wherein the binding agent comprises povidone at a concentration of 1.83% w/w of the composition, wherein the carrier comprises microcrystalline cellulose particles, and wherein the carrier is 81.36% w/w of the composition, wherein the talc is 3.34% w/w of the composition, and wherein the plasticizer comprises dibutyl sebacate at 0.67% w/w of the composition.

* * * * *